United States Patent [19]

Druliner et al.

[11] Patent Number: 5,021,395

[45] Date of Patent: Jun. 4, 1991

[54] PROCESS FOR MAKING SUPERCONDUCTORS AND THEIR PRECURSORS

[75] Inventors: Joe D. Druliner, Newark; Harold S. Horowitz, Wilmington; Stephan J. McLain, Hockessin, all of Del.; Arthur W. Sleight, Goleta, Calif.

[73] Assignee: E. I. Du Pont de Nemours and Company, Wilmington, Del.

[21] Appl. No.: 372,726

[22] Filed: Jun. 28, 1989

Related U.S. Application Data

[63] Continuation-in-part of Ser. No. 214,702, Jul. 1, 1988, abandoned.

[51] Int. Cl.$^5$ .................. H01L 39/12; C01F 17/00; C01F 11/00; C01F 1/00
[52] U.S. Cl. .................................. 505/1; 505/742; 505/737; 505/780; 505/778; 423/593; 423/604; 423/263; 423/265; 252/521; 501/123; 501/152; 502/355
[58] Field of Search .................. 505/742, 737, 1, 780, 505/778; 423/593, 604, 263, 265; 252/521; 501/123, 152; 502/355

[56] References Cited

U.S. PATENT DOCUMENTS 4,839,339 6/1989 Bunker et al. ............... 505/1
4,861,753 8/1989 McCarron, III ............. 423/593
4,943,558 7/1990 Soltis et al. .................. 505/1

OTHER PUBLICATIONS

Bednorz et al., Z. Phys. B64, 189 (1986).
Rao et al., Current Science, 56, 47 (1987).
Chu et al., Science 235, 567 (1987).
Chu et al., Phys. Rev. Lett., 58, 405 (1987).
Cava et al., Phys. Rev. Lett., 58, 408 (1987).
Bednorz et al., Europhys. Lett. 3, 379 (1987).
Wu et al., Phys. Rev. Lett., 58, 908 (1987).
Hirano et al., Chemistry Letters, 665 (1988).
Bhargava et al., Material Letters, vol. 5, Nos. 11, 12, pp. 495-497 (1987).
Takayama-Muromachi et al., Japanese Journal of Applied Physics, vol. 27, No. 2, pp. 1223-1226 (1988).
Keller et al., ACS Symposium Series, pp. 114-119, Aug. 30, 1987.
Nakamura et al., MRS, pp. 239-242, Apr. 23, 1987.
Cava et al., MRS, vol. 99, pp. 19-26, 30 Nov. 1987.
Kubo et al., MRS, vol. 99, pp. 89-94, Nov. 30, 1987.
Beyers et al., MRS, pp. 149-152, Apr. 1987.
Ito et al., Japanese Journal of Applied Physics, vol. 26, No. 5, pp. 692-693, May 1987.
Eickenbusck et al., Mat. Res. Bull., vol. 22, pp. 1505-1515 (1987).
Felner et al., Solid State Communication, vol. 66, No. 2, pp. 205-210 (1988).
Morris, et al., MRS, High Temperature Superconductors, Apr. 23-24, 1987, "Mobile Oxygen and Isotope Effect in the High Temperature Superconductor $YBa_2Cu_3O_2$", pp. 209-213.
Kubo et al., MRS, High Temp. Superconduc., Nov. 3-Dec. 4, 1987, Effect of Oxygen Pressure on the Phase Transformation in the YBaCuO and Related Superconducting Oxides pp. 89-94.
Kager, et al., MRS, High-Temp. Super., Nov. 30-Dec. 4, 1987, "Preparation of High Tc $YBa_2Cu_3O_{7-x}$ Powders from Nitrate and Oxalate Precursors", pp. 159-164.
Yamanka, et al., Japanese Journal of Applied Physics, vol. 26, No. 8, Aug., 1987, "Raman Scattering in Single Crystal $Ba_2YCu_3O_y$", pp. L1404-L1406.
Shyu, et al., MRS, vol. 99, 1988, "Annealing Effects on Properties of High Tc $YBa_2Cu_3O_{7-x}$ Ceramics" pp. 655-658.
Beyers, et al., MRS, 4/1987, "On the Relationship Between Processing, Structure, and Superconductivity in $YBa_2Cu_3O_{9-x}$", pp. 149-152.
Uno, et al., "Synthesis of Superconductive Oxides by Vacuum Calcination Method", Japanese Jr. of App. Phy., vol. 27, No. 6, Jun., 1988, pp. L1003-L1006.
Eatough, et al., "Orthorhombic-tetragonal Phase Transition in High-temperature Superconductor $YBa_2Cu_3O_7$", Appl. Phys. Lett., 51(5), Aug. 3, 1987, pp. 367-368.
Qi, et al., "Effects of Oxygen Content on the Lattice Distortions and Superconductivity in the Y-Ba-Cu-O System", Mat. Lett., vol. 5, No. 10, Sep., 1987, pp. 384-386.

*Primary Examiner*—Gary P. Straub
*Assistant Examiner*—Steven Bos

[57] ABSTRACT

A process for preparing the superconductive material $MBa_2Cu_3O_x$, M being, inter alia, yttrium and x being from about 6.5-7 and a precursor material $MBa_2Cu_3O_y$, y being from about 6-6.5, by controlled heating and cooling in a controlled atmosphere.

19 Claims, No Drawings

PROCESS FOR MAKING SUPERCONDUCTORS AND THEIR PRECURSORS

TECHNICAL FIELD AND RELATED APPLICATION

This application is a continuation-in-part of U.S. Ser. No. 214,702 filed July 1, 1988, now abandoned and relates to a low temperature process for making rare earth-barium-copper oxide superconductors and their precursors.

BACKGROUND OF THE INVENTION

Bednorz and Muller, Z. Phys. B64, 189 (1986), disclose a superconducting phase in the La-Ba-Cu-O system with a superconducting transition temperature of about 35K. The presence of this phase was subsequently confirmed by a number of investigators [see, for example, Rao and Ganguly, Current Science, 56, 47 (1987), Chu et al., Science, 235, 567 (1987), Chu et al., Phys. Rev. Lett., 58, 405 (1987), Cava et al., Phys. Rev. Lett., 58, 408 (1987), Bednorz et al., Europhys. Lett., 3, 379 (1987)]. The superconducting phase has been identified as the composition $La_{1-x}(Ba,Sr,Ca)_xO_{4-y}$ with the tetragonal $K_2NiF_4$-type structure and with x typically about 0.15 and y indicating oxygen vacancies.

Wu et al., Phys. Rev. Lett., 58, 908 (1987), disclose a superconducting phase in the Y-Ba-Cu-O system with a superconducting transition temperature of about 90 K. The compounds investigated were prepared with nominal compositions $(Y_{1-x}Ba_x)_2CuO_{4-y}$ and x=0.4 by a solid-state reaction of appropriate amounts of $Y_2O_3$, $BaCO_3$ and CuO in a manner similar to that described in Chu et al., Phys. Rev. Lett., 58, 405 (1987). This reaction method comprised heating the oxides in a reduced oxygen atmosphere of $2 \times 10^{-5}$ bars (2 Pa) at 900° C. for 6 hours. The reacted mixture was pulverized and the heating step was repeated. The thoroughly reacted mixture was then pressed into 3/16 inch (0.5 cm) diameter cylinders for final sintering at 925° C. for 24 hours in the same reduced oxygen atmosphere.

Hundreds of other papers have since disclosed similar solid state reaction processes. Other papers have disclosed various solution and precipitation methods for preparing the reactants to be heated at temperatures of 800°-850° C. and above.

Hirano et al., Chemistry Letters, 665, (1988), disclose a process for producing Y-Ba-Cu-O superconductors by the partial hydrolysis of a solution of Ba metal, Y(O-iPr)$_3$ and Cu-acetylacetonate or Cu-alkoxides in 2-methoxy or 2-ethoxy ethanol. The solution was stirred in dry nitrogen and heated at 60° C. for 12 hours. The solution was then hydrolyzed by the slow addition of water diluted with solvent. Stirring and heating continued for several hours. Stirring continued while the solution was evaporated under vacuum at about 60° C. and an amorphous precursor powder was obtained. The powder was calcined in flowing oxygen at temperatures between 800° and 950° C. for up to 24 hours. The calcined powder was pressed and sintered in flowing oxygen at temperature up to 920° C. and then annealed at temperatures between 450° and 550° C.

It is highly desirable to form precursors that can be used to produce powders that have small size particles, i.e., generally sub-micron in size, and that can be pressed into desired shapes, sintered and converted to superconducting Y-Ba-Cu-O.

SUMMARY OF THE INVENTION

This invention provides a process for preparing a powder of the tetragonal phase having the formula $MBa_2Cu_3O_y$, the orthorhombic phase having the formula $MBa_2Cu_3O_x$ or a mixture thereof, wherein M is selected from the group consisting of Y, Nd, Sm, Eu, Gd, Dy, Ho, Er, Tm, Yb, and Lu; y is from about 6.0 to about 6.5; x is from about 6.5 to about 7.0, said process consisting essentially of (a) preparing an essentially carbon-free (less than 1 weight percent) precursor powder from an intimate mixture of M, Ba and Cu compounds, said Cu in said precursor powder having a valence of 1.6-2, with an atomic ratio of M:Ba:Cu of 1:2:3;

(b) heating the precursor in an inert gas, e.g. argon, nitrogen, at a temperature from about 650° C. to about 800° C. for a time sufficient (usually about 2 hours) to form a powder of essentially tetragonal $MBa_2Cu_3O_y$; and (c) cooling said tetragonal $MBa_2Cu_3O_y$ powder in an inert or an oxygen-containing atmosphere, e.g. air, but preferably substantially pure oxygen.

It has been found that if the Cu in the Cu compound in the mixture of reactants has a valence of +1, i.e. less than 1.6, the mixtures of reactants must be heated at a temperature from about 200° C. to about 400° C. in an oxygen-containing atmosphere for from 1 to 4 hours to form the precursor used in step (b).

It should also be noted that the atomic ratio of M:Ba:Cu of 1:2:3 may not be sacrosanct. Slight variation due to the presence of impurities or weighing errors may still provide superconductive materials which, however, may not be single phase.

This invention provides a process for preparing a powder of the tetragonal phase having the formula $MBa_2Cu_3O_y$ when said tetragonal $MBa_2Cu_3O_y$ powder of step (b) is cooled in step (c) to a temperature below about 350° C., preferably below 100° C., before changing the inert atmosphere to an oxygen-containing atmosphere.

This invention provides a process for preparing a powder of the orthorhombic phase having the formula $MBa_2Cu_3O_x$ when said tetragonal $MBa_2Cu_3O_y$ powder of step (b) is cooled in step (c) to a temperature below 350° C. (to room temperature) but the inert atmosphere must be changed to an oxygen-containing atmosphere before the powder reaches a temperature of 350° C., preferably before it reaches below 400° C. The tetragonal $MBa_2Cu_3O_y$ powder can be maintained in this oxygen-containing atmosphere above 350° C. for a time sufficient to complete the transformation to the orthorhombic phase having the formula $MBa_2Cu_3O_x$.

It is preferred to have said precursor powder prepared by a solution route, for example, by drying a solution, a suspension or a precipitate of M, Ba and Cu carbon-free salts such as nitrates or hyponitrites or by drying the oxides formed by the hydrolysis of M, Ba and Cu compounds dissolved in an organic solvent.

It is also preferred to have the oxygen-containing atmosphere be free of $CO_2$.

The process of the present invention provides an especially fine powder comprising the tetragonal $MBa_2Cu_3O_y$ powder, the orthorhombic $MBa_2Cu_3O_x$ powder, and the mixed tetragonal $MBa_2Cu_3O_y$-orthorhombic $MBa_2Cu_3O_x$ powders.

The tetragonal $MBa_2Cu_3O_y$ powder and the mixture of tetragonal $MBa_2Cu_3O_y$ and orthorhombic $MBa_2$-

$Cu_3O_x$ powders can be converted to a powder of the orthorhombic phase having the formula $MBa_2Cu_3O_x$ by heating the tetragonal $MBa_2Cu_3O_y$ powder or the mixture in an oxygen-containing atmosphere at a temperature from about 350° C. to about 800° C., preferably 350° C. to 600° C., and maintaining the powder in the oxygen-containing atmosphere while cooling but maintaining the temperature above 350° C. for a time sufficient to obtain the orthorhombic phase.

The tetragonal $MBa_2Cu_3O_y$ powder, the orthorhombic $MBa_2Cu_3O_x$ powder or the mixed tetragonal $MBa_2Cu_3O_y$-orthorhombic $MBa_2Cu_3O_x$ powders can be pressed into a desired shape, sintered at a temperature from about 875° C. to about 950° C. in an oxygen-containing atmosphere, and maintained in an oxygen-containing atmosphere while cooling for a time sufficient to obtain a superconducting shaped product comprised of orthorhombic $MBa_2Cu_3O_x$, wherein x is from about 6.5 to about 7.0, preferably from about 6.8 to about 7.0.

DETAILED DESCRIPTION OF THE INVENTION

This invention provides a relatively low temperature process for preparing a powder of the tetragonal phase having the formula $MBa_2Cu_3O_y$, the orthorhombic phase having the formula $MBa_2Cu_3O_x$ or a mixture thereof, wherein M is selected from the group consisting of Y, Nd, Sm, Eu, Gd, Dy, Ho, Er, Tm, Yb, and Lu; y is from about 6.0 to about 6.5; and x is from about 6.5 to about 7.0. This unique process makes it possible to produce a powder of orthorhombic superconducting phase $MBa_2Cu_3O_x$, with x preferably from about 6.8 to about 7.0, with maximum process temperatures of 650° C. and a single heating.

The tetragonal $MBa_2Cu_3O_y$ powder, the orthorhombic $MBa_2Cu_3O_x$ powder and the mixed tetragonal $MBa_2Cu_3O_y$-orthorhombic $MBa_2Cu_3O_x$ powder can all be produced by this process with primary particle size in the micron or sub-micron range. All of these powders are therefore very useful for producing sintered shaped superconducting articles which are dense since these small particles sinter better than those containing larger size particles typical of powders made using conventional higher temperature solid state reactions. The process of this invention is useful in producing other oxide powders for sintering and, in particular, in producing oxide powders that can be used to make other oxide superconductors such as those containing Bi.

The reactants used in the process of this invention must be of the type and form that will react at temperatures below 800° C. by this process to form tetragonal $MBa_2Cu_3O_y$. It is necessary to avoid the use of $BaCO_3$ as a reactant in the process and to avoid the formation of $BaCO_3$ during the process since the presence of $BaCO_3$ necessitates reaction temperatures of at least about 900° C. While air can be used when an oxygen-containing atmosphere is required in the process of this invention, it is preferred to use an oxygen-containing atmosphere that is free of $CO_2$.

The process of this invention uses an essentially carbon-free precursor powder containing an intimate mixture of M, Ba and Cu compounds with an atomic ratio of M:Ba:Cu of 1:2:3. As used herein, essentially carbon-free means that there is less than 1 wt % carbon in the precursor powder. The precursor powder must be an intimately mixed fine-particle powder in order to facilitate the low temperature solid state reaction that it undergoes during the process. A solution route for the preparation of the precursor powder yields an intimately mixed fine-particle powder and solution-derived precursor powders are preferred.

The precursor powder used in this invention can be prepared by drying a solution or suspension containing M, Ba and Cu compounds with an atomic ratio of M:Ba:Cu of 1:2:3. One method for preparing such precursor powder is to form a nitrate solution of M, Ba and Cu, for example, by simply mixing aqueous solutions of the three component nitrates. This solution can be dried directly by heating, by spray-drying, or by spray-freezing followed by freeze-drying. Alternatively, precipitation can be achieved and a suspension formed by increasing the pH of the solution. The suspension can then be dried as indicated above. Spray-drying or spray-freezing followed by freeze-drying are preferred since they provide a more intimately mixed powder.

Another method for preparing the precursor powder is to form an aqueous nitrate solution of M, Ba and Cu with an atomic ratio of M:Ba:Cu of 1:2:3, mix it with an excess of a hyponitrite solution such as sodium hyponitrite or sodium peroxide to form a precipitate containing essentially all of the M, Ba and Cu present in the original nitrate solution, and collect and dry the precipitate.

Still another method for preparing the precursor powder is to form a solution of M, Ba and Cu compounds with an atomic ratio of M:Ba:Cu of 1:2:3 in an organic solvent. Controlled hydrolysis results in the formation of oxides, or hydrous oxides, which when filtered, washed and dried serve as the precursor powder. Compounds suitable to form the solution must satisfy two criteria. They must be soluble in an organic solvent and they must react readily with water to produce metal oxide or metal hydroxide. The following list is not meant to be limiting but some of the types of compounds which meet these criteria and representative examples are metal alkyls such as $Cu(CH_2SiMe_3)$ and $Y(CH_2SiMe_3)_3$, metal cyclopentadienides such as $Y(C_5H_5)_3$, $Ba(C_5H_5)_2$ and $Ba(C_5Me_5)_2$, metal acetylides such as $Cu[C\equiv CC(CH_3)_2OMe]$, metal aryls such as Cu(mesityl), metal alkoxides such $Cu(OCMe_3)$, $Cu[OCH(CMe_3)_2]$, $Cu(OCH_2CH_2OBu)_2$, $Cu(OCH_2CH_2NEt_2)_2$, $Y_5O(OCHMe_2)_{13}$, $Y(OCH_2CH_2OBu)_3$, $Y(OCH_2CH_2NEt_2)_3$, $Ba(OCHMe_2)_2$, $Ba(OCH_2CH_2OBu)_2$ and $Ba(OCH_2CH_2NEt_2)_2$, metal aryloxides such $Y[O-2,4,6-C_6H_2(CMe_3)_3]_3$, and metal amides such as $Cu(NEt_2)$, $Cu(NBu_2)$, $Cu[N(SiMe_3)_2]$ and $Y[N(SiMe_3)_2]_3$.

If the Cu in the Cu compound in the reactant mixture has a valence of +1, the mixture should be heated to a temperature from about 200° C. to about 400° C. in an oxygen-containing atmosphere for from 1 to 4 hours to form the precursor powder. Such treatment is typically sufficient to raise the valence of the Cu to the necessary range of 1.6 to 2. The valence of the Cu can be determined by iodimetric titration. If the valence is less than 1.6, it can be raised to the necessary range by heating the mixture for a longer time to a temperature from about 200° C. to about 400° C. in an oxygen-containing atmosphere to form the precursor powder.

The precursor powder is placed in an inert container or an inert tray, for example, on an alumina tray, and heated in an inert gas, such as argon or nitrogen, at a temperature from about 650° C. to about 800° for a time sufficient to form a powder comprised of tetragonal $MBa_2Cu_3O_y$, wherein y is from about 6.0 to about 6.5.

Two hours has proven to be sufficient time to form the tetragonal $MBa_2Cu_3O_y$ but longer times can be used.

The tetragonal $MBa_2Cu_3O_y$ powder is then cooled in an inert or an oxygen-containing atmosphere. The nature of the final product depends on the cooling program.

When the tetragonal $MBa_2Cu_3O_y$ powder is cooled to a temperature below 350° C., preferably below 100° C., before changing the inert atmosphere to an oxygen-containing atmosphere, the product powder is tetragonal $MBa_2Cu_3O_y$ powder.

When the tetragonal $MBa_2Cu_3O_y$ powder is cooled to a temperature below 350° C. and the inert atmosphere is changed to an oxygen-containing atmosphere before the powder reaches a temperature of 350° C., and the tetragonal $MBa_2Cu_3O_y$ powder is maintained in this oxygen-containing atmosphere at a temperature above 350° C. for a sufficient time, the product powder can convert completely to the orthorhombic $MBa_2Cu_3O_x$ powder. During the cooling step, the oxygen content of the material increases to give the desired $MBa_2Cu_3O_x$ product. The additional oxygen which enters into the crystalline lattice of the material during this cooling step to form the desired product does so by diffusion. The rate at which oxygen enters the lattice is determined by a complex function of time, temperature, oxygen content of atmosphere, sample form, etc. Consequently, there are numerous combinations of these conditions that will result in the desired product. For example, the rate of oxygen uptake by the material at 500° C. is rapid, and the desired product can be obtained in less than an hour under these conditions when the sample is in the form of a loosely packed, fine particle powder. A convenient way to accomplish the conversion is to allow the powder to cool in the furnace to a temperature below 100° C. before it is removed. If the cooling has been carried out too rapidly to accomplish complete conversion, the powder can be reheated to a temperature above 350° C., from about 350° C. to about 800° C., preferably 350° C. to 600° C., in an oxygen-containing atmosphere and maintained at this temperature above 350° C. for a longer time sufficient to obtain the orthorhombic $MBa_2Cu_3O_x$ phase. Other cooling programs generally result in mixed tetragonal $MBa_2Cu_3O_y$-orthorhombic $MBa_2Cu_3O_x$ powder.

As suggested above, the tetragonal $MBa_2Cu_3O_y$ powder or the mixed tetragonal $MBa_2Cu_3O_y$-orthorhombic $MBa_2Cu_3O_x$ powder can be converted to a powder of only the orthorhombic phase having the formula $MBa_2Cu_3O_x$ by heating the tetragonal $MBa_2Cu_3O_y$ powder or the mixed tetragonal $MBa_2Cu_3O_y$-orthorhombic $MBa_2Cu_3O_x$ powder in an oxygen-containing atmosphere at a temperature from about 350° C. to about 800° C., preferably 350° C. to 600° C., and maintaining the powder in an oxygen-containing atmosphere while cooling for a time sufficient to obtain the orthorhombic phase.

These product powders, i.e., the tetragonal $MBa_2Cu_3O_y$ powder, the orthorhombic $MBa_2Cu_3O_x$ powder and the mixed tetragonal $MBa_2Cu_3O_y$-orthorhombic $MBa_2Cu_3O_x$ powder, are typically composed of primary particles the majority of which are sub-micron in size as determined by scanning and transmission electron microscopy. When prepared using an organic solvent, the sizes range from 0.02 to 0.2 micron; by using other methods, 0.1 to 3 microns. Any of these powders can be pressed into a desired shape, sintered at a temperature from about 875° C. to about 950° C. in an oxygen-containing atmosphere, and maintained in an oxygen-containing atmosphere while cooling for a time sufficient to obtain a superconducting dense shaped product comprised of orthorhombic $MBa_2Cu_3O_x$, wherein x is from about 6.5 to about 7.0, preferably from about 6.8 to about 7.0. Well sintered shaped articles will take longer to form the desired product while cooling than will powders, and larger, well-sintered shaped articles may require many hours.

These product powders can be stored and then pressed and sintered when desired. However, they all display the same reactivity toward $CO_2$ and $H_2O$ as has been reported for the orthorhombic phase. Hence, appropriate precautions must be taken.

The presence of superconductivity can be determined by the Meissner effect, i.e., the exclusion of magnetic flux by a sample when in the superconducting state. This effect can be measured by the method described in an article by E. Polturak and B. Fisher in *Physical Review B*, 36, 5586 (1987). It is well known that particles with dimensions of the order of or less than the penetration depth do not exhibit flux exclusion. Particles of the powders of this invention are typically sub-micron and with estimates of the penetration depth of these materials of the same order of magnitude, i.e., 0.1-1.0 μm, at 77K, the absence or weakening of the Meissner effect for these particles is to be expected. Because of the temperature dependence of the penetration depth, a depressed value of Tc might also be anticipated.

The superconducting compositions of this invention can be used to conduct current extremely efficiently or to provide a magnetic field for magnetic imaging for medical purposes. Thus, by cooling the composition in the form of a wire or bar to a temperature below the superconducting transition temperature, by exposing the material to liquid nitrogen or liquid helium in a manner well known to those in this field, and initiating a flow of electrical current, one can obtain such flow without any electrical resistive losses. To provide exceptionally high magnetic fields with minimal power losses, the wire mentioned previously could be wound to form a coil which would be exposed to liquid helium or nitrogen before inducing any current into the coil. Magnetic fields provided by such coils can be used to levitate objects as large as railroad cars. These superconducting compositions are also useful in Josephson devices such as SQUIDS (superconducting quantum interference devices) and in instruments that are based on the Josephson effect such as high speed sampling circuits and voltage standards.

The copper alkoxides $Cu(OCH_2CH_2OBu)_2$ and $Cu(OCH_2CH_2NEt_2)_2$ used as Cu source compounds in the hydrolysis preparation of the precursor powder are novel compounds. They fall within the group of copper alkoxides with 2-substituted ethoxy groups, the 2-substituent being XR, where X is a heteroatom such as O, N, S or P and R is an alkyl group. These novel soluble alkoxide compounds of copper with copper in the oxidation state +2 have the formula $Cu[(OCH_2CH_2)_nOR]_2$ where when n=1, R is an alkyl group of C4 or larger, and when n≧2 R is an alkyl group of C1 or larger; $Cu(OCH_2CH_2NR_2)_2$ where R is an alkyl group of C1 or larger; $Cu(OCH_2CH_2SR)_2$ where R is an alkyl group of C4 or larger, and $Cu(OCH_2CH_2PR_2)_2$ where R is a phenyl group, a substituted phenyl group or an alkyl group of C4 or larger. The alkyl group can be straight-chain or branched and the substituted phenyl can contain any non-acidic functional group. These alkoxides can be prepared by the methods shown in Examples 11-19. Preferred for use in the preparation of the precursor powder are $Cu[(OCH_2CH_2)_nOR]_2$ and $Cu(OCH_2CH_2NR_2)_2$ because of their solubilities of more than 0.1 g/mL in toluene and in tetrahydrofuran (THF). Especially preferred is $Cu(OCH_2CH_2NR_2)_2$ because it is also volatile and can be prepared free of chloride. In addition to their use as copper sources in the preparation of the precursor powder, they are also useful for copper plating.

In the Examples describing the preparation and characterization of these alkoxides, the following procedures were followed. The THF and toluene used were dried by distillation from sodium benzophenone ketyl. All solvents were stored over activated zeolite 4A in a drybox. Solubilities in toluene and THF are reported as the weight of compound in 1.00 mL of a saturated solution and as mmol Cu/liter (M) for a saturated solution. Although all these alkoxides are very soluble in methylene chloride, qualitative solubilities could not be measured because of the high viscosity of the concentrated solutions. NMR spectra were recorded at 300 MHz and are reported in parts per million downfield of Me$_4$Si.

EXAMPLES OF THE INVENTION

EXAMPLE 1

A Y/Ba/Cu hyponitrite precursor powder was prepared as follows. A Y-Ba-Cu nitrate solution was formed by mixing $Y(NO_3)_3 \cdot 6H_2O$ (1.92 g, 5 mmole), $Ba(NO_3)_2$ (2.92 g, 11 mmole), $Cu(NO_3)_2 \cdot 3H_2O$ (3.86 g, 16 mmole) and ice water (500 cc) in a 1 L Erlenmeyer flask using a Teflon ®-coated stir bar. The solids almost completely dissolved upon stirring. The flask was kept in a wet ice bath. A solution of $Na_2N_2O_2$ (15 g, 142 mmole) in ice water (50 cc) was prepared in a 100 mL Erlenmeyer flask and this flask was also kept in a wet ice bath. The Y-Ba-Cu nitrate solution was stirred briskly as the $Na_2N_2O_2$ solution was added to it. A green precipitate formed immediately. The precipitate was collected by filtration, air dried for about fifteen minutes, and then dried under full vacuum (less than 0.1 mm Hg, i.e., less than 13 Pa) overnight to give 6.92 g of a fine, light green powder. Analyses for Y, Ba, Cu, and N were done and the following results obtained:

|  | Y | Ba | Cu | N |
|---|---|---|---|---|
| wt % | 6.10 | 19.5 | 13.1 | 5.06 |
| Atomic ratio | 1 | 2.07 | 3.00 | 5.26 |

Within experimental error, a molecular formula of $YBa_2Cu_3(N_2O_2)_2 \cdot 6(OH)_aO_b$ is consistent with the analytical results, "a" and "b" being undetermined but providing the desirable amount of oxygen in the final product.

A portion (0.31 g) of this precursor powder was spread in a thin layer in an alumina tray and fired at 700° C. in argon for 2 hours. The furnace was turned off and the sample allowed to cool in argon to below 100° C. before being removed from the furnace. The resulting powder was black and the yield was 0.19 g. An X-ray diffraction powder pattern of the material showed that the powder was predominantly tetragonal $YBa_2Cu_3O_y$. There were also traces of $BaCuO_2$ and an unidentified phase.

EXAMPLE 2

A portion (0.83 g) of the precursor powder prepared in Example 1 was spread in a thin layer in an alumina tray and heated to 700° C. in argon. The temperature was maintained at 700° C. for 2 hours, after which it was lowered to 600° C. The atmosphere was then switched from argon to oxygen and the sample was held at 600° C. in oxygen for 2 hours. The furnace was turned off and the sample allowed to cool in oxygen to below 100° C. before being removed from the furnace. The resulting product was a black powder and the yield was 0.65 g. An X-ray diffraction powder pattern of the material showed that the product was orthorhombic $YBa_2Cu_3O_x$ with a trace of $BaCuO_2$. Magnetic flux exclusion measurements confirmed superconductivity and showed the sample to have a Tc onset of about 50 K.

EXAMPLE 3

A portion (0.18 g) of the precursor powder prepared in Example 1 was spread in a thin layer in an alumina tray and heated to 700° C. in argon. The temperature was maintained at 700° C. for about 15 hours, after which the furnace was turned off and the sample allowed to cool in argon to below 100° C. before being removed from the furnace. The resulting powder was black and the yield was 0.09 g. An X-ray diffraction powder pattern showed that the powder was single phase, tetragonal $YBa_2Cu_3O_y$.

A portion (0.06 g) of this tetragonal $MBa_2Cu_3O_y$ powder was heated at 400° C. in oxygen for 2 hours, after which the furnace was turned off and the sample allowed to cool in oxygen to below 100° C. before being removed from the furnace. An X-ray diffraction powder pattern showed that the product was single phase, orthorhombic $YBa_2Cu_3O_x$. Magnetic flux exclusion measurements confirmed superconductivity and showed the sample to have a Tc onset of about 82 K.

CONTROL A

Criticality of Inert Atmosphere in Step (b)

A portion (0.09 g) of the precursor powder prepared in Example 1 was spread in a thin layer in an alumina tray and heated to 700° C. in oxygen. The temperature was maintained at 700° C. for about 16 hours, after which the furnace was turned off and the sample allowed to cool in oxygen below 100° C. before being removed from the furnace. The resulting product was a black powder, and the yield was 0.05 g. An X-ray diffraction powder pattern showed that the product consisted of $BaCuO_{2.5}$ as the major phase plus second phases of $YBa_2Cu_3O_x$ and unidentified products. This result demonstrates that a direct low temperature (700° C.) decomposition of the hyponitrite precursor powder in an oxidizing atmosphere will not yield a substantially pure $YBa_2Cu_3O_x$ phase.

EXAMPLE 4

A Y/Ba/Cu nitrate precursor powder was prepared as follows. $Ba(NO_3)_2$ (12.54 g, 0.048 moles) was dissolved in 150 mL of distilled water. $Y(NO_3)_3 \cdot 6H_2O$ (9.22 g, 0.024 moles) was dissolved in about 20 mL of distilled water. These two solutions were added together. To this combined colorless solution was added a $Cu(NO_3)_2$ solution (57.186 g, 0.072 moles) which was prepared by dissolving 23.0 g of hydrated $Cu(NO_3)_2$ in 55 mL distilled water and analyzed by iodimetric titration as 8.0 wt % copper. The resulting solution was dark blue and the pH of the solution was 2.67. $NH_4OH$ was then added dropwise until the pH was increased to pH 6.5. Precipitation started as the pH reached about 3.3 and a light blue, fine suspension had formed when the pH reached 6.5. This suspension was then sprayed through an air atomization nozzle into a covered beaker containing liquid nitrogen. The nozzle, manufactured by Spraying Systems Co., Wheaton, Ill., was Model 9265-J-LUC fitted with fluid cap #2850-LUC, liquid orifice diameter of 0.028 in (0.7 mm) and air cap #70-LUC. The nozzle was pressurized by 20 psi (140 kPa) of air. The resulting slurry of liquid nitrogen and finely divided frozen powder was then freeze dried. The powder obtained was light blue and very fluffy. The yield was 33.9 g. An X-ray diffraction powder pattern of the material showed an unidentified crystalline phase(s).

A portion (0.71 g) of this freeze dried precursor powder was spread in a thin layer in an alumina tray and heated to 700° C. in argon. The temperature was maintained at 700° C. for 2 hours, after which the furnace was turned off and the sample allowed to cool in argon to below 100° C. before being removed from the furnace. The resulting powder was medium gray and the yield was 0.31 g. An X-ray diffraction powder pattern showed that the powder consisted of tetragonal $YBa_2Cu_3O_y$ as the major phase with minor amounts of $BaCuO_2$, $CuO$ and $YBa_3Cu_2O_7$.

EXAMPLE 5

A portion (0.35 g) of the precursor powder made in Example 4 was spread in a thin layer in an alumina tray and heated to 700° C. in argon. The temperature was maintained at 700° C. for 2 hours, after which the temperature was lowered to 600° C. The atmosphere was then switched from argon to oxygen and the sample was held at 600° C. in oxygen for 2 hours. The furnace was turned off and the sample allowed to cool below 100° C. in oxygen before being removed from the furnace. The resulting product was a black powder and the yield was 0.15 g. An X-ray diffraction powder pattern of the material showed that the product consisted of orthorhombic $YBa_2Cu_3O_x$ as the major phase with minor amounts of $BaCuO_2$, $CuO$ and $YBa_3Cu_2O_7$. Magnetic flux exclusion measurements confirmed superconductivity and showed the sample to have a Tc of about 66 K.

CONTROL B

A portion (1.08 g) of the precursor powder described in Example 4 was spread in a thin layer in an alumina tray and heated to 700° C. in oxygen. The temperature was maintained at 700° C. for about 16 hours, after which the furnace was turned off and the sample allowed to cool in oxygen to below 100° C. before being removed from the furnace. The resulting sample was greyish-black and an X-ray diffraction powder pattern showed that the product consisted of $BaCuO_{2.5}$ as the major phase with minor amounts of $CuO$, $Y_2O_3$ and an unidentified phase(s). This result demonstrates that a direct low temperature (700° C.) decomposition of the nitrate precursor powder in an oxidizing atmosphere will not yield the $YBa_2Cu_3O_x$ phase.

EXAMPLE 6

A Y/Ba/Cu reactant powder was prepared by combining $Y(OCHMe_2)_3$ (0.532 g, 2.00 mmol), $Ba(OCHMe_2)_2$ (1.02 g, 4.00 mmol), and $Cu(OCMe_3)$ (0.820 g, 6.00 mmol) in 15 ml of 95% tetrahydrofuran (THF)/5% isopropanol to give a clear solution. Hydrolysis was carried out by dropwise addition of this solution to a solution of degassed water (1.80 g, 100 mmol) in 10 ml of 95% THF/5% isopropanol. The mixture was refluxed under an argon atmosphere for 16 h, and filtered to give an orange solid. The solid was washed first with THF, then with ether, and dried under vacuum at 150° C. An X-ray diffraction powder pattern indicated the presence of $Cu_2O$ and unidentified phases of Y, Ba and possibly Cu.

A portion (0.19 g) of this reactant powder was spread in a thin layer in an alumina tray and heated to 300° C. for 2 hours in oxygen to increase the copper valence from the precursor powder. The atmosphere was then switched to argon and the temperature raised to 700° C. The temperature was maintained at 700° C. for 2 hours, after which the furnace was turned off and the sample allowed to cool in argon below 100° C. before being removed from the furnace. The resulting powder was black, and the yield was 0.17 g. An X-ray diffraction powder pattern showed that the powder consisted of tetragonal $YBa_2Cu_3O_y$ as the major phase with trace amounts of $Y_2BaCuO_5$, $BaCuO_2$ and $CuO$.

A portion of this tetragonal $MBa_2Cu_3O_y$, powder (0.14 g) was subsequently heated to 600° C. in oxygen. The temperature was maintained at 600° C. for 2 hours, after which the furnace was turned off and the sample allowed to cool in oxygen below 100° C. before being removed. The resulting powder was unchanged in appearance and the yield was 0.16 g. The X-ray diffraction powder pattern showed that the product consisted of orthorhombic $YBa_2Cu_3O_x$ and trace amounts of $Y_2BaCuO_5$ and $CuO$.

EXAMPLE 7

A Y/Ba/Cu precursor powder was prepared by combining $Y(OCHMe_2)_3$ (1.60 g, 6.00 mmol), $Ba(OCHMe_2)_2$ (3.06 g, 12.0 mmol) and $Cu(NBu_2)$ (3.45 g, 18.0 mmol) in 50 ml of THF to give a clear solution. Hydrolysis was carried out by dropwise addition of this solution to a solution of degassed water (5.40 g, 300 mmol) in 40 ml of THF. The mixture was refluxed under an argon atmosphere for 16 hours, and filtered to give an orange solid. The solid was washed first with THF, then with ether, and dried under high vacuum at 100° C. An X-ray diffraction powder pattern indicated the presence of $Cu_2O$ and unidentified phases of Y, Ba and possibly Cu.

A portion (0.77 g) of this precursor powder was spread in a thin layer in an alumina tray and heated to 300° C. for 2 hours in oxygen to increase the copper valence above 1.0. The atmosphere was then switched to argon and the temperature raised to 650° C. The temperature was maintained at 650° C. for 12 hours, after which the furnace was turned off and the sample allowed to cool in argon below 100° C. before being removed from the furnace. The resulting powder was black and the yield was 0.65 g. An X-ray diffraction powder pattern showed that the powder was tetragonal $YBa_2Cu_3O_y$ with a trace of $BaCuO_2$.

A portion (0.35 g) of this tetragonal $MBa_2Cu_3O_y$ powder of the above product was subsequently heated to 400° C. in oxygen. The temperature was maintained at 400° C. for 14 hours, after which the furnace was turned off and the sample allowed to cool in oxygen to below 100° C. before being removed from the furnace. The resulting powder was black and the yield was 0.34 g. An X-ray diffraction powder pattern showed the product was comprised of orthorhombic $YBa_2Cu_3O_x$ and a trace of $BaCuO_2$.

Measurement down to 4 K. showed no signs of magnetic flux exclusion. The negative result may be attributable to the extremely fine particle size of the $YBa_2Cu_3O_x$. For particles with radii equal to or less than the magnetic flux penetration depth, l, there will be no flux exclusion. l is temperature dependent, although the nature of this dependence is not well defined. At 77 K., however, it is assumed that l may be as large as 0.5 $\mu$m. Scanning electron micrographs show that the primary particle size of this sample is less than 0.2 $\mu$m and, thus, the particles would not be expected to exclude flux.

There is expected to be an enhancement of the flux exclusion effect subsequent to particle growth which occurs at sintering temperatures. In order to demonstrate this effect, a portion of the orthorhombic, but non-flux excluding $YBa_2Cu_3O_x$ described above was heated at 950° C. for 4 hours in oxygen. Scanning electron microscopy showed that the particles had grown to ~1 $\mu$m. Magnetic flux exclusion measurements showed the sample to be superconducting with a $Tc=92K$. It was also discovered that annealing the orthorhombic, but non-flux excluding $YBa_2Cu_3O_x$ at 600° C. in $O_2$ for 15 hours results in superconducting transition at 90 K. which was weak due to the limited growth of particles.

EXAMPLE 8

A Y/Ba/Cu precursor powder was prepared by stirring Ba metal (0.861 g, 6.27 mmol) in 25 ml of 2-butoxyethanol until hydrogen evolution was complete. $Y(OCHMe_2)_3$ (0.834 g, 3.13 mmol) was added, and the solution was heated to 120° C. and then cooled to 80° C. $Cu(OCH_2CH_2OBu)_2$ (2.80 g, 9.40 mmol) as prepared in Example 11 was added, and the hot solution was filtered. The 2-butoxyethanol was removed in vacuo, and the blue solid was redissolved in 35 ml of THF. The THF solution was added dropwise to a solution of water (2.82 g, 157 mmol) in 35 ml of THF. The mixture was refluxed under an argon atmosphere for 16 hours, and filtered to give a brown solid. The solid was washed first with THF, then with ether, and dried under high vacuum at 100° C.

A portion (0.30 g) of this precursor powder was spread in a thin layer on an alumina tray and heated to 700° C. for 2 hours in argon. The sample was then allowed to cool in argon below 100° C. before being removed from the furnace. The resulting powder was black and the yield was 0.26 g. An X-ray diffraction powder pattern showed that the powder was tetragonal $YBa_2Cu_3O_y$ with a minor amount of an unidentified phase(s).

A portion (0.19 g) of this tetragonal $MBa_2Cu_3O_y$ powder was subsequently heated to 600° C. for 2 hours in oxygen, after which the furnace was turned off and the sample allowed to cool in oxygen to below 100° C. before being removed from the furnace. The resulting powder was black and the yield was 0.18 g. An X-ray diffraction powder pattern showed the product was comprised of orthorhombic $YBa_2Cu_3O_x$ and trace amounts of CuO and $BaCO_3$ along with a minor amount of an unidentified phase. Magnetic flux exclusion measurements showed the sample to be superconducting with $Tc=62$ K. Scanning electron microscopy showed that the primary particles were in the range 0.5–3.0 $\mu$m.

EXAMPLE 9

A Y/Ba/Cu reactant powder was prepared by a procedure essentially identical to that used in Example 7, except that an equimolar amount of Cu(mesityl) was substituted for $Cu(NBu_2)$, Cu having a valence of 1.

A portion (0.35 g) of the reactant powder was spread in a thin layer on an alumina tray and heated to 300° C. for 2 hours in oxygen to increase the copper valence and form the precursor powder. The atmosphere was then switched to argon and the temperature raised to 700° C. The temperature was maintained at 700° C. for 2 hours, after which the furnace was turned off and the sample allowed to cool in argon below 100° C. before being removed from the furnace. The resulting powder was black and the yield was 0.31 g. An X-ray diffraction powder pattern showed that the powder was tetragonal $YBa_2Cu_3O_y$ with minor amounts of $BaCuO_2$ and $Y_2BaCuO_5$.

A portion (0.23 g) of the tetragonal $MBa_2Cu_3O_y$ powder was subsequently heated to 400° C. in oxygen. The temperature was maintained at 400° C. for 4 hours, after which the furnace was turned off and the sample allowed to cool in oxygen to below 100° C. before being removed from the furnace. The resulting powder was black and the yield was 0.22 g. An X-ray diffraction powder pattern showed that the product was orthorhombic $YBa_2Cu_3O_x$ with trace amounts of $BaCuO_2$ and $Y_2BaCuO_5$. No magnetic flux exclusion was observed down to 4 K. This result may be attributed to fine particle size.

EXAMPLE 10

A Y/Ba/Cu precursor powder was prepared by stirring Ba metal (0.516 g, 3.76 mmol) in a solution of 15 ml of N,N-diethylethanolamine and 25 ml of toluene at 100° C. until hydrogen evolution was complete. $Y(OCHMe_2)_3$ (0.500 g, 1.88 mmol) was added and the solution was maintained at 100° C. for 10 minutes, and then cooled to room temperature. $Cu(OCH_2CH_2NEt_2)_2$ (1.67 g, 5.63 mmol) was added, and the solution was filtered. The solvents were removed in vacuo, and the purple oil was redissolved in 25 ml of THF. The THF solution was added dropwise to a solution of water (1.69 g, 93.3 mmol) in 25 ml of THF. The mixture was refluxed under an argon atmosphere for 16 hours, and filtered to give a brown solid. The solid was washed first with THF, then with ether, and dried under high vacuum at 100° C.

A portion (0.22 g) of this precursor powder was spread in a thin layer on an alumina tray and heated to 650° C. in argon. The temperature was maintained at 650° C. for about 15 hours, after which the furnace was turned off and the sample allowed to cool in argon below 100° C. before being removed from the furnace. The resulting powder was greyish-brown and the yield was 0.19 g. An X-ray diffraction powder pattern showed that the powder was tetragonal $YBa_2Cu_3O_y$ along with minor amounts of $BaCuO_2$ and CuO.

A portion of the tetragonal $MBa_2Cu_3O_y$ powder (0.08 g) was subsequently heated to 400° C. in oxygen. The temperature was maintained at 400° C. for 4 hours, after which the furnace was turned off and the sample allowed to cool in oxygen to below 100° C. before being removed from the furnace. The resulting powder was dark brown and the yield was 0.08 g. An X-ray diffraction powder pattern showed that the product was orthorhombic $YBa_2Cu_3O_x$ with minor amounts of $BaCuO_2$ and CuO.

EXAMPLE 11

$Cu(OCH_2CH_2OBu)_2$ was prepared as follows. $Cu(OMe)_2$ (2.00 g, 15.9 mmol) was combined with 10 mL of 2-butoxyethanol and 40 mL of toluene, and heated to 100° C. for 15 minutes. The warm solution was filtered and the solvent removed in vacuo to give 4.21 g dark blue solid which was $Cu(OCH_2CH_2OBu)_2$. The proton nuclear magnetic resonance (NMR) spectrum is characteristic of an antiferromagnetically coupled Cu(II) compound. The proton resonances are well resolved, featureless peaks. The $CH_2$ protons closest to the paramagetic Cu(II) have an unusually large chemical shift. The NMR results are: 1H NMR ($C_6D_6$ 300 MHz, ppm downfield of $Me_4Si$): 2.45 (t,$CH_3$); 3.19 (s,$CH_2$); 5.94 (s,$CH_2$); 7.00 (s,$CH_2$); 109.1 (s,$CH_2$).

A solution of 0.050 g of $Cu(OCH_2CH_2OBu)_2$ in 1.0 mL of toluene was combined with a solution of 0.055 g freshly distilled cyclopentadiene ($C_5H_6$). Within 30 minutes a metallic copper mirror had formed on the walls of the glass vial.

EXAMPLE 12

$Cu(OCH_2CH_2NEt_2)_2$ was prepared as follows. $Cu(OMe)_2$ (2.00 g, 15.9 mmol) was combined with 10 mL of N,N-diethylethanoloamine and 40 mL of toluene, and heated to 100° C. for 15 minutes. The warm solution was filtered and the solvents were removed in vacuo to give a solid. Sublimation of the crude product at 100° C. in high vacuum gave 2.86 g blue-green solid which was $Cu(OCH_2CH_2NEt_2)_2$. This compound has an electron spin resonance spectrum typical of a monomeric Cu(II) complex.

A solution of $Cu(OCH_2CH_2NEt_2)_2$ in 1.0 mL of N,N-diethylethanolamine was combined with a solution of 0.05 g freshly distilled cyclopentadiene ($C_5H_6$) in 1.0 mL of N,N-diethylethanolamine. After 16 hours a metallic copper mirror had formed on the walls of the glass vial.

EXAMPLE 13

$Cu(OCH_2CH_2NEt_2)_2$ was prepared as follows. Lithium metal wire [0.826 g, 119 mmol] was stirred in dry methanol until the reaction was complete to give a homogeneous solution of lithium methoxide. The solution was added dropwise to a solution of $CuCl_2$ [8.00 g, 59.5 mmol] in 250 mL of methanol. The mixture was stirred for 2 days and then filtered to give light blue solid $Cu(OMe)_2$. The product was washed with MeOH until the filtrates showed no detectable chloride by reaction with $AgBF_4$ in THF, and dried briefly in vacuo. $Cu(OMe)_2$ was combined with 15.3 g of N,N-diethylethanolamine in 100 mL of toluene and heated to 100° C. for 15 minutes to give a homgeneous purple solution. The solvents were removed in vacuo and the resulting solid was sublimed at 100° C., $10^{-3}$ torr to give a turquoise solid which was $Cu(OCH_2CH_2NEt_2)_2$. The yield was 13.38 g (76%). The expected weight percentages of the component elements in this alkoxide calculated on the basis of the formula $C_{12}H_{28}CuN_2O_2$ are: C, 48.71; H, 9.54; N, 9.47; Cu, 21.5. The weight percentages of the component elements found in two separate analyses of the product were: C, 48.54, 48.84; H, 9.46, 9.57; N, 9.60, 9.53; Cu, 21.4, 21.4; Cl, <0.2. The melting point was found to be 126°-128° C. The electron spin resonance (ESR) results (2-methylpentane, 120 K.) are: g(parallel)=2.192, a<Cu>=158 G, g(perpendicular)=2.142. These results are consistent with monomeric Cu(II).

The solubility in THF is 0.268 g/mL (0.91M). The solubility in toluene is 0.248 g/mL (0.83M).

EXAMPLE 14

$Cu(OCH_2CH_2NMe_2)_2$ was prepared by the same procedure used in Example 13 to prepare $Cu(OCH_2CH_2NEt_2)_2$ except that dimethylethanol was used instead of N,N-diethylethanolamine. The yield was 52%. The expected weight percentages of the component elements in this alkoxide calculated on the basis of the formula $C_8H_{20}CuN_2O_2$ are: C, 40.07; H, 8.41; N, 11.7; Cu, 26.5. The weight percentages of the component elements found in two separate analyses of the product were: C, 40.23, 40.25; H, 8.49, 8.57; N, 11.6, 11.6; Cu, 26.2, 25.9; Cl, <0.2. The melting point was found to be 93°-94° C.

The solubility in THF and toluene is qualitatively similar to that of $Cu(OCH_2CH_2NEt_2)_2$.

EXAMPLE 15

$Cu(OCH_2CH_2OBu)_2$ was prepared as follows. $Cu(OMe)_2$ [2.00 g, 15.9 mmol] prepared as described in Example 13 was combined with 2-butoxyethanol [4.52 g, 38.2 mmol] and 40 mL of toluene, and heated to 100° C. for 15 min. The warm solution was filtered and the solvents were remove in vacuo to a give a dark blue solid which was recrystallized by dissolving in a minimal amount of toluene, and cooling to $-40°$ C. to produce $Cu(OCH_2CH_2OBu)_2$. The yield was 3.10 g (65%). The expected weight percentages of the component elements in this alkoxide calculated on the basis of the formula $C_{12}H_{26}CuO_4$ are: C, 48.39; H, 8.80; Cu, 21.3. The weight percentages of the component elements found in two separate analyses of the product were: C, 47.11, 47.10; H, 7.75, 7.88; Cu, 21.7, 21.7; Cl, 0.64, 0.63. None of the samples of this compound was completely free of chloride. The expected weight percentages of the component elements in this alkoxide calculated on the basis of the formula $CuC_{10.05}(OCH_2CH_2OBu)_{1.95}$ are: C, 47.81; H, 8.69; Cu, 21.6; Cl, 0.63.

The NMR results are ($C_6H_6$): 1.582(s, $CH_3$); 2.450(s, $CH_2$); 3.182(s, $CH_2$); 5.936(s, $CH_2$); 6.40(s, $CH_2$); 109.12(s, $CH_2$).

The solubility in THF is 0.160 g/mL (0.54M). The solubility in toluene is 0.102 g/mL (0.34M).

EXAMPLE 16

$Cu(OCH_2CH_2OCH_2CHMe_2)_2$ was prepared by the same procedure used in Example 15 to prepare $Cu(OCH_2CH_2OBu)_2$ except that 2-isobutoxyethanol was used instead of 2-butoxyethanol. The yield without recrystallization was 85%. The expected weight percentages of the component elements in this alkoxide calculated on the basis of the formula $C_{12}H_{26}CuO_4$ are: C, 48.39; H, 8.80; Cu, 21.3. The weight percentages of the component elements found in two separate analyses of the product were: C, 48.35, 48.37; H, 8.66, 8.70; Cu, 21.9, 22.0.

The solubility in THF and toluene is qualitatively similar to that of $Cu(OCH_2CH_2OBu)_2$.

EXAMPLE 17

$Cu(OCH_2CH_2OCH_2CH_2OEt)_2$ was prepared by the same procedure used in Example 15 to prepare $Cu(OCH_2CH_2OBu)_2$ except that 2-ethoxyethoxylethanol was used instead of 2-butoxyethanol. The yield without recrystallization was 84%. The expected weight percentages of the component elements in this alkoxide calculated on the basis of the formula $C_{12}H_{26}CuO_6$ are: C, 43.69; H, 7.94; Cu, 19.3. The weight percentages of the component elements found in two separate analyses of the product were: C, 41.74, 41.51; H, 7.44, 7.44; Cu, 19.5, 19.6. The NMR results are $(C_6D_6)$: 1.67(t, 4.3H, $CH_3$); 4.16(q, 1.9H, $CH_2$); 5.12(s, 1.7H, $CH_2$); 6.35(s, $CH_2$); 6.84(s, $CH_2$). One $CH_2$ resonance is missing and presumably it is outside the normal chemical shift range (see 1H NMR of $Cu(OCH_2CH_2OBu)_2$ above).

The solubility in THF and toluene is qualitatively similar to that of $Cu(OCH_2CH_2OBu)_2$.

EXAMPLE 18

$Cu(OCH_2CH_2SBu)_2$ was prepared by the same procedure used in Example 15 to prepare $Cu(OCH_2CH_2OBu)_2$ except that N-butylthioethanol was used instead of 2-butoxyethanol. Following recrystallization from toluene, the dark blue solid $Cu(OCH_2CH_2SBu)_2$ product was obtained. The yield was 76%. The expected weight percentages of the component elements in this alkoxide calculated on the basis of the formula $C_{12}H_{26}CuO_2S_2$ are: C, 43.68; H, 7.94; Cu, 19.3. The weight percentages of the component elements found in two separate analyses were: C, 43.90, 43.79; H, 7.90, 7.77; Cu, 19.0, 18.6; Cl, <0.2. The solubility of $Cu(OCH_2CH_2SBu)_2$ in THF was 0.007 g/mL (0.02M). $Cu(OCH_2CH_2SBu)_2$ was essentially insoluble in toluene. It dissolves readily in methylene chloride.

EXAMPLE 19

$Cu(OCH_2CH_2PPh_2)_2$ was prepared as follows. $Cu(OMe)_2$ [0.100 g, 0.80 mmol] prepared as described in Example 13 was combined with $Ph_2PCH_2CH_2OH$ [0.403 g, 1.75 mmol] and 40 mL of toluene, and heated to 100° C. for 5 min. The warm solution was filtered and the solvents were removed in vacuo to a give a pale green solid which was recrystallized by dissolving in a minimal amount of ether, and cooling to −40° C. to produce $Cu(OCH_2CH_2PPh_2)_2$. The yield was 0.233 g (56%). The expected weight percentages of the component elements in this alkoxide calculated on the basis of the formula $C_{28}H_{28}CuO_2P_2$ are: C, 64.42; H, 5.41; Cu, 12.2; P, 11.9. The weight percentages of the component elements found in two separate analyses were: C, 64.42, 64.42; H, 5.52, 5.49; Cu, 10.7, 10.7; P, 12.3, 12.3; Cl, 0.42, 0.50.

$Cu(OCH_2CH_2PPh_2)_2$ has only slight solubility in THF or toluene. It dissolves readily in methylene chloride.

CONTROL C

Attempts to prepare a sample of $Cu(OCH_2CH_2OEt_2)_2$ by the same procedure used to produce $Cu(OCH_2CH_2OBu)_2$ in Example 15, except that 2-ethoxyethanol was used instead of 2-butoxyethanol, resulted in a product that was essentially completely insoluble in toluene, THF, and 2-ethoxyethanol. The compound was purified by dissolving it in $CH_2Cl_2$, filtering the solution, and removing the solvent in vacuo. The yield was 70%. The expected weight percentages of the component elements in this formula $C_8H_{18}CuO_4$ are: C, 39.74; H, 7.50; Cu, 26.3. The weight percentages of the component elements found in two separate analyses were: C, 37.83, 37.89; H, 7.22, 7.22; Cu, 27.1, 27.4.

A more soluble form of this compound was prepared by stirring $Cu(OMe)_2$ [1.50 g, 11.9 mmol] prepared as described in Example 13 in a mixture of 25 mL of 2-ethoxyethanol and 60 mL of toluene for 1 hour at room temperature. The mixture was filtered to remove an insoluble green gel, and the dark blue filtrate was concentrated in vacuo to give a blue solid which was now insoluble in toluene, 2-ethoxyethanol, or mixtures of the two. This product was recrystallized by dissolving in a minimal amount of THF and cooling the filtered solution to −40° C. The yield was 1.28 g (44%). The expected weight percentages of the component elements in this alkoxide calculated on the basis of the formula $C_8H_{18}CuO_4$ are: C, 39.74; H, 7.50; Cu, 26.3. The weight percentages of the component elements found in two separate analyses were: C, 39.27, 38.24; H, 7.70, 7.44; Cu, 26.3, 26.4; Cl, 0.46, 0.45. The expected weight percentages of the component elements in this alkoxide calculated on the basis of the formula $CuC_{10.0-3}(OCH_2CH_2OEt)_{1.97}$ are: C, 39.41; H, 7.44; Cu, 26.5; Cl, 0.44. The solubility in THF is 0.074 g/mL (0.31M). The solubility in toluene is 0.007 g/mL (0.02M). It is essentially insoluble in 2-ethoxyethanol.

EXAMPLE 20

A Y/Ba/Cu precursor powder was prepared by combining $Y(OCHMe_2)_3$ (1.799 g, 6.76 mmol), $Ba(OCHMe_2)_2$ (3.454 g, 13.5 mmol), and $Cu(OCH_2CH_2NEt_2)_2$ (6.00 g, 20.3 mmol) in 80 mL of THF to give a clear solution. Hydrolysis was carried out by dropwise addition of this solution to a solution of degassed water (7.914 g, 439 mmol) in 80 mL of THF. The mixture was refluxed under an argon atmosphere for 16 hours, and filtered to give a dark brown solid. The solid was washed first with THF, then with pentane, and dried under high vacuum at 100° C.

Firing this precursor for 12 hours at 700° C. in flowing argon yielded a single phase, tetragonal $YBa_2Cu_3O_y$ powder as determined by X-ray diffraction. This tetragonal powder was subsequently annealed at 400° C. in flowing oxygen for 12 hours. The X-ray diffraction powder pattern indicated that the oxidized powder was orthorhombic $YBa_2Cu_3O_x$. The value of x was measured by iodimetric titration to be 6.86.

Subsequently it has been learned (see, e.g., D. C. Bradley, *J. Chem. Soc. Chem. Commun.* 1258, (1988) that the correct stoichiometry of the yttrium alkoxide is not $Y(OCHMe_2)_3$, but rather $Y_5O(OCHMe_2)_{13}$. Preparation of the Y/Ba/Cu precursor powder using the proper stoichiometry for the alkoxide results in small improvements in the purity of the $YBa_2Cu_3O_y$ and $YBa_2Cu_3O_x$ products.

EXAMPLE 21

A Y/Ba/Cu precursor powder was prepared as follows. A Y-Ba-Cu nitrate solution was formed by mixing $Y(NO_3)_3 \cdot 6H_2O$ (0.384 g, 1.0 mmole), $Ba(NO_3)_2$ (1.2 g, 4.5 mmol), $Cu(NO_3)_2 \cdot 3H_2O$ (0.726 g, 3.0 mmole) and ice water (100 mL) in a 500 mL Erlenmeyer flask using a Teflon ®-coated stir bar. The solids almost completely dissolved upon stirring. The flask was kept in a wet ice bath. A solution of $Na_2O_2$ (2.18 g, 28 mmole) in ice water (100 mL) was prepared in a 250 mL Erlenmeyer flask and this flask was also kept in a wet ice bath. The Y-Ba-Cu nitrate solution was added to it. A dark green precipatate formed immediately. After about one minute of stirring, the precipitate was collected by centrifugation, in a chilled tube (5° to 10° C.), at 3,000 rpm for 12 minutes. The wet solids were dried under full vacuum (less than 0.1 mm Hg, i.e., less than 13 Pa) overnight to give 0.59 g of a fine light blue powder. Analyses for Y, Ba, and Cu were done and the following results obtained:

|  | Y | Ba | Cu |
|---|---|---|---|
| wt % | 9.08 | 28.3 | 19.3 |
| Atomic ratio | 1 | 2.02 | 2.98 |

A portion of precursor powder prepared essentially by this method was spread in a thin layer in an alumina tray and fired at 700° C. in argon for 12 hours. The resulting powder was black and an X-ray diffraction powder pattern of the material indicated that it consisted of tetragonal $YBa_2Cu_3O_y$, along with trace amounts of $Y_2BaCuO_5$ and $BaCuO_2$.

What is claimed is:

1. A process for preparing a powder of the tetragonal phase having the formula $MBa_2Cu_3O_y$, wherein
M is selected from Y, Nd, Sm, Eu, Gd, Dy, Ho, Er, Tm, Yb and Lu; and
y is from about 6 to about 6.5, said process consisting essentially of the following steps:
   (a) forming an essentially carbon-free precursor powder of compounds of M, Ba and Cu, said Cu in the precursor powder having a valence of 1.6 to 2, by a process comprising mixing compounds of M, Ba and Cu, the quantities of said compounds in the mixture so formed being such as to provide an atomic ratio of M:Ba:Cu of 1:2:3;
   (b) heating said precursor powder in the presence of an inert gas to a temperature of about 650° C. to about 800° C.;
   (c) maintaining said temperature above 650° C. for a time sufficient to provide a powder of the tetragonal phase having the formula $MBa_2Cu_3O_y$; and
   (d) cooling the powder formed in step (c) to a temperature below 350° C. in an inert atmosphere.

2. A process for preparing a powder comprising the orthorhombic phase having the formula $MBa_2Cu_3O_x$, wherein M is selected from the group consisting of Y, Nd, Sm, Eu, Gd, Dy, Ho, Er, Tm, Yb and Lu; and x being from about 6.5 to about 7, consisting essentially of the following steps:
   (a) forming an essentially carbon-free precursor powder of compounds of M, Ba and Cu, said Cu in the precursor powder having a valence of 1.6 to 2, by a process comprising mixing compounds of M, Ba and Cu, the quantities of said compounds in the mixture so formed being such as to provide an atomic ratio of M:Ba:Cu of 1:2:3;
   (b) heating said precursor powder in the presence of an inert gas to a temperature of about 650° C. to about 800° C.;
   (c) maintaining said temperature above 650° C. for a time sufficient to provide a powder of the tetragonal phase having the formula $MBa_2Cu_3O_y$ wherein y is from about 6 to about 6.5; and
   (d) cooling the powder formed in step (c) in an oxygen-containing atmosphere and maintaining said powder in said oxygen-containing atmosphere at a temperature of at least 350° C. for a time sufficient to transform at least a portion of said tetragonal phase to the orthorhombic phase.

3. The process of claim 2 wherein said oxygen-containing atmosphere is free of $CO_2$.

4. A process for preparing a powder comprising the orthorhombic phase having the formula $MBa_2Cu_3O_x$, wherein M is selected from the group consisting of Y, Nd, Sm, Eu, Gd, Dy, Ho, Er, Tm, Yb, and Lu; and x being from about 6.5 to about 7, consisting essentially of the following steps:
   (a) forming an essentially carbon-free precursor powder of compounds of M, Ba and Cu, said Cu in the precursor powder of compounds of M, Ba and Cu, said Cu in the precursor powder having a valence of 1.6 to 2, by a process comprising mixing compounds of M, Ba and Cu, the quantities of said compounds in the mixture so formed being such as to provide an atomic ratio of M:Ba:Cu of 1:2:3;
   (b) heating said precursor powder in the presence of an inert gas to a temperature of about 650° C. to about 800° C.;
   (c) maintaining said temperature above 650° C. for a time sufficient to provide a powder of the tetragonal phase having the formula $MBa_2Cu_3O_y$ wherein y is from about 6 to about 6.5;
   (d) cooling the powder formed in step (c) to a temperature below 350° C. in an inert atmosphere; and
   (e) reheating the powder resulting from step (d) to a temperature from about 350° C. to about 600° C. in an oxygen-containing atmosphere and maintaining said powder in said oxygen-containing atmosphere at a temperature of at least 350° C. for a time sufficient to transform at least a portion of said tetragonal phase to the orthorhombic phase.

5. The process of claim 4 wherein said oxygen-containing atmosphere is free of $CO_2$.

6. The process as in claim 1 wherein the valence of said Cu in said mixture formed in step (a) has a value of 1 and said mixture is heated at a temperature of about 200° C. to 400° C. in an oxygen-containing atmosphere to form said precursor powder having Cu having a valence in the range of 1.6 to 2.

7. The process of claim 6 wherein said oxygen-containing atmosphere is free of $CO_2$.

8. The process as in claim 1 wherein Cu in said compound of Cu in said mixture formed in step (a) has a valence of 2.

9. The process as in claim 1 wherein M is yttrium.

10. The process as in claim 2 wherein the powder formed in step (c) is maintained at a temperature of at least 400° C. in an oxygen-containing atmosphere for a time sufficient to convert the material in the tetragonal phase to the orthorhombic phase.

11. The process of claim 10 wherein said oxygen-containing atmosphere is free of $CO_2$.

12. The process of claim 4 wherein said powder resulting from step (d) is reheated to a temperature of at least 400° C. in an oxygen-containing atmosphere for a time sufficient to convert the material in the tetragonal phase to the orthorhombic phase.

13. The process as in claim 12 wherein said oxygen-containing atmosphere is free of $CO_2$.

14. The process of claim 1 wherein the inert gas is argon or nitrogen and the inert atmosphere consists essentially of argon or nitrogen.

15. The process of claim 14 wherein the inert gas is argon and the inert atmosphere consists essentially of argon.

16. The process of claim 2 wherein the inert gas is argon or nitrogen and the inert atmosphere consists essentially of argon or nitrogen.

17. The process of claim 16 wherein the inert gas is argon and the inert atmosphere consists essentially of argon.

18. The process of claim 4 wherein the inert gas is argon or nitrogen and the inert atmosphere consists essentially of argon or nitrogen.

19. The process of claim 18 wherein the inert gas is argon and the inert atmosphere consists essentially of argon.

* * * * *